United States Patent
Hikage et al.

(10) Patent No.: US 9,068,945 B2
(45) Date of Patent: Jun. 30, 2015

(54) SURFACE PLASMON-FIELD ENHANCED FLUORESCENCE SPECTROSCOPIC MEASUREMENT METHOD AND SURFACE PLASMON-FIELD ENHANCED FLUORESCENCE SPECTROSCOPIC MEASUREMENT DEVICE

(75) Inventors: Naoki Hikage, Tokyo (JP); Masataka Matsuo, Tokyo (JP); Takatoshi Kaya, Tokyo (JP)

(73) Assignee: KONICA MINOLTA, INC. (JP)

( * ) Notice: Subject to any disclaimer, the term of this patent is extended or adjusted under 35 U.S.C. 154(b) by 0 days.

(21) Appl. No.: 14/126,752

(22) PCT Filed: May 31, 2012

(86) PCT No.: PCT/JP2012/064089
§ 371 (c)(1),
(2), (4) Date: Dec. 16, 2013

(87) PCT Pub. No.: WO2012/172987
PCT Pub. Date: Dec. 20, 2012

(65) Prior Publication Data
US 2014/0117255 A1    May 1, 2014

(30) Foreign Application Priority Data

Jun. 17, 2011  (JP) .................. 2011-135511

(51) Int. Cl.
*G01N 21/64*      (2006.01)
*G01N 33/543*    (2006.01)
(Continued)

(52) U.S. Cl.
CPC .............. *G01N 21/64* (2013.01); *G01N 21/648* (2013.01); *G01N 2021/6417* (2013.01);
(Continued)

(58) Field of Classification Search
CPC ......................................................... G01N 4/64
USPC ........................................ 250/459.1, 458, 0.1
See application file for complete search history.

(56) References Cited

U.S. PATENT DOCUMENTS 7,361,472 B2    4/2008    Yguerabide et al.
8,107,071 B2    1/2012    Kimura
(Continued)

FOREIGN PATENT DOCUMENTS

JP    2004-77294 A    3/2004
JP    2009-79970 A    4/2009
(Continued)

OTHER PUBLICATIONS

Extended European Search Report Issued in connection with the corresponding application No. 12800555.0., Issued Jun. 25, 2014.
(Continued)

*Primary Examiner* — Kiho Kim
(74) *Attorney, Agent, or Firm* — Cantor Colburn LLP

(57) ABSTRACT

To provide a surface plasmon-field enhanced fluorescence spectroscopic measurement method and a surface plasmon-field enhanced fluorescence spectroscopic measurement device which are capable of accurately measuring a fluorescent signal regardless of the type of a light detection means even when the concentration of an analyte is high by adjusting the dynamic range of the SPFS device. A surface plasmon-field enhanced fluorescence stereoscopic measurement method wherein an analyte labeled with a fluorescent substance is excited by surface plasmon light generated by applying excitation light to a metallic thin film, and generated fluorescence is received by a light detection means to thereby detect the analyte. The dynamic range is expanded by adjusting the amount of the fluorescence received by the light detection means.

10 Claims, 11 Drawing Sheets

(51) Int. Cl.
  *B01L 3/00*   (2006.01)
  *G01N 33/58*  (2006.01)

(52) U.S. Cl.
  CPC ........ *G01N 2021/6439* (2013.01); *G01N 2021/6482* (2013.01); *G01N 33/54373* (2013.01); *B01L 3/502715* (2013.01); *B01L 2300/0654* (2013.01); *B01L 2300/0816* (2013.01); *B01L 2300/168* (2013.01); *G01N 33/582* (2013.01)

(56) References Cited

U.S. PATENT DOCUMENTS

| | | |
|---|---|---|
| 2009/0015831 A1 | 1/2009 | Yguerabide et al. |
| 2009/0079978 A1 | 3/2009 | Kimura |
| 2011/0239438 A1* | 10/2011 | Ogawa ............................ 29/464 |
| 2013/0078148 A1 | 3/2013 | Kaya et al. |

FOREIGN PATENT DOCUMENTS

| | | |
|---|---|---|
| JP | 2009-244270 A | 10/2009 |
| JP | 2009-270931 A | 11/2009 |
| WO | 2008142492 A1 | 11/2008 |
| WO | 2010134470 A1 | 11/2010 |
| WO | 2011155435 A1 | 12/2011 |

OTHER PUBLICATIONS

International Search Report for International Application No. PCT/JP2012/064089, mailed Jul. 3, 2012.

Written Opinion of the Interational Searching Authority for International Application No. PCT/JP2012/064089, mailed Jul. 3, 2012, with English translation.

\* cited by examiner

SURFACE PLASMON-FIELD ENHANCED FLUORESCENCE SPECTROSCOPIC MEASUREMENT METHOD AND SURFACE PLASMON-FIELD ENHANCED FLUORESCENCE SPECTROSCOPIC MEASUREMENT DEVICE

CROSS REFERENCE TO RELATED APPLICATIONS

This is the U.S. national stage of application No. PCT/JP2012/064089, filed on 31 May 2012. Priority under 35 U.S.C. §119 (a) and 35 U.S.C. §365(b) is claimed from Japanese Application No. 2011-135511, filed 17 Jun. 2011, the entirety of which is also incorporated herein by reference.

TECHNICAL FIELD

The present invention relates to a surface plasmon-field enhanced fluorescence spectroscopic measurement method and a surface plasmon-field enhanced fluorescence spectroscopic measurement apparatus based on a principle of a surface plasmon-field enhanced fluorescence spectroscopy (SPFS) for putting a surface plasmon resonance (SPR) phenomenon to practical use.

BACKGROUND ART

In the case in which a detection of an extremely fine substance is carried out, a wide variety of specimen material detection apparatus has been used for enabling an inspection of such a substance by putting a physical phenomenon of a substance to practical use from the past.

As one of such specimen material detection apparatuses, there can be mentioned for instance a surface plasmon resonance apparatus (hereafter referred to as an SPR apparatus) in which a phenomenon of a resonance of an electron and a light in a minute region of a nanometer level or the like (a surface plasmon resonance (SPR) phenomenon) is put to practical use and an extremely fine analyte in a biological body is detected for instance.

As one of such specimen material detection apparatuses, there also can be mentioned for instance a surface plasmon-field enhanced fluorescence spectroscopic measurement apparatus (hereafter referred to as an SPFS apparatus) in which the analyte detection can be carried out with a higher degree of accuracy as compared with the SPR apparatus based on a principle of a surface-plasmon enhanced fluorescence spectroscopy (SPFS) for putting a surface plasmon resonance (SPR) phenomenon to practical use.

For the surface-plasmon enhanced fluorescence spectroscopy (SPFS), under the condition of the attenuated total reflectance (ATR) of an excitation light such as a laser light that has been applied from the light source on a surface of a metallic thin film, by generating a surface plasmon light (a crude density wave) on a surface of a metallic thin film, a photon amount that is included in an excitation light that has been applied from the light source is increased by several ten times to several hundred times to obtain an electric field enhancement effect of a surface plasmon light.

By the electric field enhancement effect, a fluorescence substance that has been coupled (labeled) with an analyte that has been captured near a metallic thin film is excited in an efficient manner. By observing the fluorescence while using a light detection means such as a photomultiplier tube (PMT) of a photon counting system and a charge coupled device (CCD) camera, an analyte of an infinitesimal quantity and/or an extremely low concentration is detected in the above method.

PRIOR ART DOCUMENTS

Patent Literature

[Patent Literature 1]
Japanese Patent Application Laid-Open Publication No. 2009-79970
[Patent Literature 2]
Japanese Patent Application Laid-Open Publication No. 2009-244270

SUMMARY OF INVENTION

Problems to be Solved by the Invention

However, in the case of an SPFS apparatus that is provided with high sensitivity in which an analyte is integrated in an assay area (a measurement region), a fluctuation range of a fluorescence signal (a signal that is output from a light detection means) is extremely large as compared with a change of a concentration of an analyte.

Consequently, in the case in which a concentration of an analyte is high, a dynamic range is exceeded for a light detection means such as a photomultiplier tube and a CCD camera, whereby a measurement cannot be carried out in a precise manner in some cases.

In the case of a camera in which an imaging element such as a CCD is used for instance, as shown in FIG. 14, in the case in which a light of a certain level or higher is received, a light receiving element is saturated and an actual amount of fluorescence cannot be measured unfortunately. In addition, in the case in which a photomultiplier tube of a photon counting system is used, as shown in FIG. 15, in the case in which a light of a certain level or higher is received, a count loss caused by a pulse overlap occurs and a fluorescence signal is reduced unfortunately.

The Patent Literature 1 discloses that a dynamic range is tried to be expanded by changing an area of a measurement region on a sample plate in order to restrict a number of substances to be analyzed in a measurement volume.

The Patent Literature 2 discloses a wide variety of methods for expanding a dynamic range such as a method in which a dynamic range of a specimen material analysis is expanded by synthesizing a plurality of signals that are provided with different exposure time and a calculation and a processing of a signal for quantifying an integrated light.

However, for the method that is disclosed in the Patent Literature 1, a measurement region that is provided with a different area is required in accordance with a concentration of an analyte, whereby an SPFS apparatus will be growing in size. Or every when an analyte that is provided with a different concentration is measured, it is necessary to prepare a sample plate in which a measurement region that is provided with a different area is formed.

On the other hand, as a problem peculiar to an SPFS apparatus, in the case in which a fluorescence labeled substance is linked to an analyte that has been integrated in an assay area, a fluorescence substance is closely spaced in a limited area, whereby a concentration quenching occurs and a fluorescence signal is reduced. Or a fluorescence that has been emitted from a fluorescence substance that has been linked to an analyte is coupled to a surface plasmon light that has been generated on a surface of a metallic thin film, causing a loss of the fluorescence signal in some cases.

It is important in order to secure the accuracy of an SPFS apparatus to discriminate whether the loss of the fluorescence signal occurs on a metallic thin film or a fluorescence signal is reduced by a problem of a dynamic range of a light detection means. However, the inventions that have been disclosed in the Patent Literatures 1 and 2 is not necessarily related to an expansion of a dynamic range that is suitable for an SPFS apparatus in a practical sense.

The present invention was made in consideration of such conditions, and an object of the present invention is to provide a surface plasmon-field enhanced fluorescence spectroscopic measurement method and surface plasmon-field enhanced fluorescence spectroscopic measurement apparatus that are capable of measuring a fluorescence signal in a precise manner regardless of a type of a light detection means by adjusting a dynamic range of an SPFS apparatus even in the case in which a concentration of an analyte is high.

Means for Solving the Problems

The present invention was made in order to solve the problems of the conventional art described above and achieve the purpose.

A surface plasmon-field enhanced fluorescence spectroscopic measurement method in accordance with the present invention is characterized by comprising the steps of exciting a fluorescence substance that has labeled an analyte by surface plasmon light that has been generated by applying an excitation light to a metallic thin film and receiving the generated fluorescence by a light detection means to thereby detect the analyte, wherein:

a dynamic range is expanded by adjusting a light amount of the fluorescence that is received by the light detection means.

A surface plasmon-field enhanced fluorescence spectroscopic measurement apparatus in accordance with the present invention that is configured to carry out a detection of a specimen material by applying an excitation light, in which a metallic thin film that is formed on a dielectric member, a fine flow passage that is formed on an upper surface of the metallic thin film, and a sensor chip that is provided with a sensor part that is formed in the fine flow passage are mounted, is characterized by comprising:

a light source that is configured to apply an excitation light to the metallic thin film via the dielectric member; and a light detection means that is disposed over the sensor chip, wherein the light detection means is configured to receive a fluorescence that is generated by exciting a fluorescence substance that labels an analyte that is fixed to the sensor part by a surface plasmon light that is generated in the case in which the excitation light is applied to the metallic thin film; and a fluorescence amount adjusting means is configured to be able to adjust a light amount of a fluorescence that is received by the light detection means.

By this configuration, in the case in which a detection of a specimen material solution that is provided with a high concentration of an analyte is carried out, even in the case in which a fluorescence that is provided with a light amount that cannot be measured by the light detection means is emitted from a fluorescence substance, a measurement can be carried out in a precise manner by adjusting an amount of a fluorescence that is received by the light detection means, and a detection of an analyte that is provided with a wide dynamic range can be carried out in a precise manner.

In addition, for the present invention, since a light amount of a fluorescence that is received by the light detection means is adjusted, a detection of an analyte that is provided with a wide dynamic range can be carried out in a precise manner regardless of a type of a light detection means.

The surface plasmon-field enhanced fluorescence stereoscopic measurement method in accordance with the present invention is characterized by further comprising the steps of:

by comparing a first fluorescence signal that is output in the case in which the light detection means receives a fluorescence under a first condition and a second fluorescence signal that is output in the case in which the light detection means receives a fluorescence in which a light amount has been adjusted under a second condition in which a light amount of a fluorescence that is received by the light detection means is adjusted so as to be smaller than that in the first condition, judging whether or not the first fluorescence signal is abnormal; and obtaining a normal fluorescence signal by correcting the second fluorescence signal in the case in which it is decided that the first fluorescence signal is abnormal.

The surface plasmon-field enhanced fluorescence spectroscopic measurement apparatus in accordance with the present invention is characterized in that:

by comparing a first fluorescence signal that is output in the case in which the light detection means receives a fluorescence under a first condition and a second fluorescence signal that is output in the case in which the light detection means receives a fluorescence in which a light amount has been adjusted by the fluorescence amount adjusting means under a second condition in which a light amount of a fluorescence that is received by the light detection means is adjusted so as to be smaller than that in the first condition, it is judged whether or not the first fluorescence signal is abnormal; and a normal fluorescence signal is obtained by correcting the second fluorescence signal in the case in which it is decided that the first fluorescence signal is abnormal.

By this configuration, even in the case in which a fluorescence that is provided with a light amount that cannot be measured by the light detection means is emitted from a fluorescence substance, a normal fluorescence signal can be obtained by using a second fluorescence signal that is output in the case in which the light detection means receives a fluorescence in which a light amount has been adjusted.

Consequently, a detection can be carried out in a precise manner for specimen material solutions including a specimen material solution that is provided with a high concentration of an analyte and a specimen material solution that is provided with a low concentration of an analyte, and a detection of an analyte that is provided with a wide dynamic range can be carried out.

The surface plasmon-field enhanced fluorescence stereoscopic measurement method in accordance with the present invention is characterized by further comprising the step of adjusting a light amount of a fluorescence that is received by the light detection means by adjusting a light amount of the fluorescence that has been generated.

The surface plasmon-field enhanced fluorescence spectroscopic measurement apparatus in accordance with the present invention is characterized in that the fluorescence amount adjusting means is disposed between the sensor chip and the light detection means.

By this configuration, a fluorescence that is emitted by exciting a fluorescence substance by a surface plasmon light can be adjusted in a direct way, and it is easy to reduce a light amount to be a light amount that can be measured by the light detection means.

The surface plasmon-field enhanced fluorescence stereoscopic measurement method in accordance with the present invention is characterized by further comprising the step of adjusting a light amount of a fluorescence that is received by the light detection means by adjusting a light amount of the excitation light.

The surface plasmon-field enhanced fluorescence spectroscopic measurement apparatus in accordance with the present invention is characterized in that the fluorescence amount adjusting means is disposed between the light source and the dielectric member.

Even in the case of this configuration, the intensity of an electrical field by a surface plasmon light can be reduced by reducing a light amount of the excitation light that is applied to the metallic thin film, and as a result, a light amount of a fluorescence that is emitted from a fluorescence substance that labels an analyte can be reduced to be a light amount that can be measured by the light detection means.

The surface plasmon-field enhanced fluorescence stereoscopic measurement method in accordance with the present invention is characterized by further comprising the step of:

receiving a fluorescence by the light detection means while changing an incidence angle of the excitation light to the metallic thin film in a predetermined range; and judging an abnormal fluorescence signal based on the relationship between an incidence angle of the excitation light and a fluorescence signal that is output in the case in which the light detection means receives a fluorescence.

The surface plasmon-field enhanced fluorescence spectroscopic measurement apparatus in accordance with the present invention is characterized in that:

a fluorescence is received by the light detection means while changing an incidence angle of the excitation light to the metallic thin film in a predetermined range by using the application angle adjusting means; and an abnormal fluorescence signal is judged based on the relationship between an incidence angle of the excitation light and a fluorescence signal that is output in the case in which the light detection means receives a fluorescence.

Even in the case of this configuration, in the case in which a fluorescence that is provided with a light amount that cannot be measured by the light detection means is emitted from a fluorescence substance, it can be decided that an abnormal fluorescence signal is output from the light detection means.

Advantageous Effects of Invention

By the present invention, a measurement can be carried out in a precise manner and an analyte that is provided with a wide dynamic range that is suitable for a surface plasmon-field enhanced fluorescence spectroscopic measurement method or a surface plasmon-field enhanced fluorescence spectroscopic measurement apparatus by adjusting an amount of a fluorescence that is received by a light detection means by using a fluorescence amount adjusting means even in the case in which a fluorescence that exceeds a measurement enable range of a light detection means is generated.

DESCRIPTION OF EMBODIMENTS

An embodiment (example) of the present invention will be described below in more detail with reference to the drawings.

Embodiment 1

Figure 1:
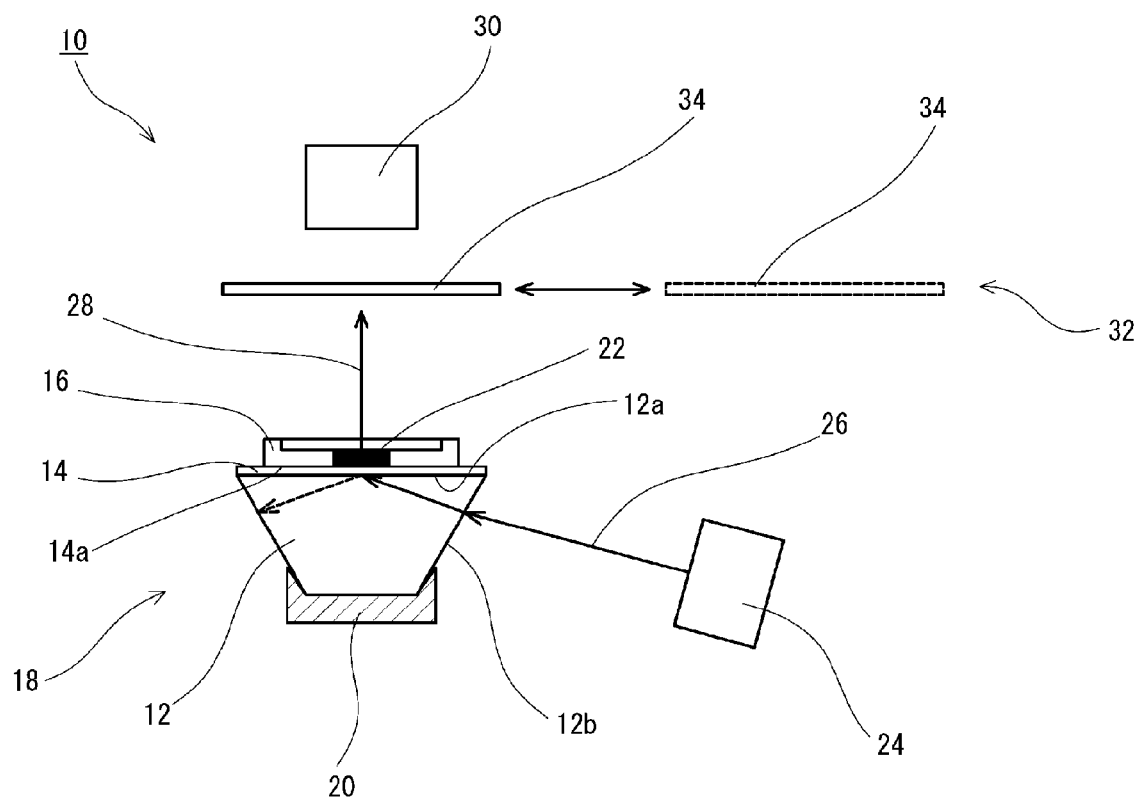
FIG. 1 is a schematic plan view showing a frame format of a simple overview of a surface plasmon-field enhanced fluorescence spectroscopic measurement apparatus for describing a surface plasmon-field enhanced fluorescence spectroscopic measurement method in accordance with an embodiment of the present invention.
Figure 2:
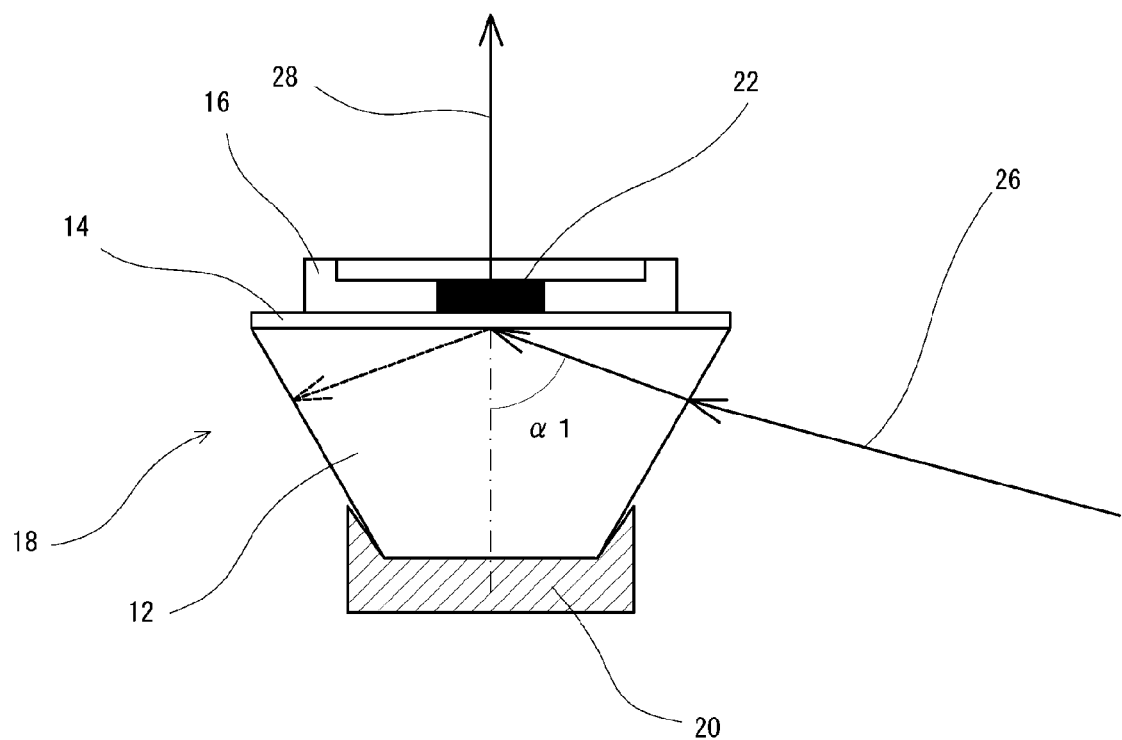
FIG. 2 is a partially enlarged view of FIG. 1.
Figure 3:
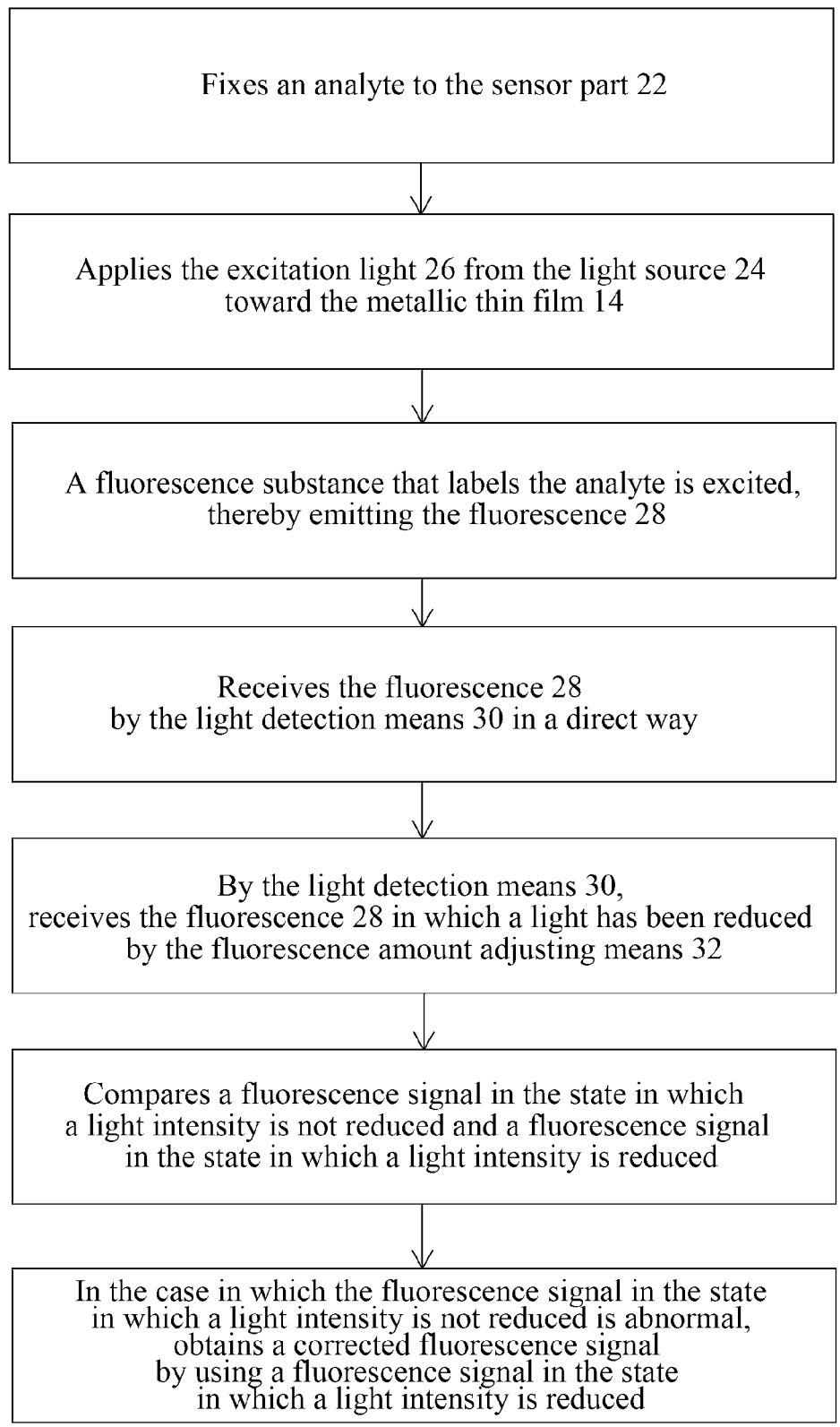
FIG. 3 is a flowchart for illustrating a flow of a surface plasmon-field enhanced fluorescence spectroscopic measurement.

1. Embodiment in the Case in which a Light Amount of a Fluorescence that has been Generated is Adjusted FIG. 1 is a schematic plan view showing a frame format of a simple overview of a surface plasmon-field enhanced fluorescence spectroscopic measurement apparatus (hereafter referred to as an SPFS apparatus) for describing a surface plasmon-field enhanced fluorescence spectroscopic measurement method in accordance with an embodiment of the present invention. FIG. 2 is a partially enlarged view of FIG. 1. FIG. 3 is a flowchart for illustrating a flow of a surface plasmon-field enhanced fluorescence spectroscopic measurement.

1-1. Configuration of the SPFS Apparatus

An SPFS apparatus 10 in accordance with the present invention is provided with a sensor chip 18 that is composed of a dielectric member 12 in a prism shape in which a vertical cross sectional shape is a generally trapezoidal shape, a metallic thin film 14 that is formed on a horizontal upper surface 12a of the dielectric member 12, and a fine flow passage 16 that is formed on a horizontal upper surface 14a of the metallic thin film 14. The sensor chip 18 is mounted to a sensor chip mounting part 20 of the SPFS apparatus 10.

Moreover, a sensor part 22 to which a ligand that is linked to a particular analyte in a specific manner has been fixed is formed at a part of the fine flow passage 16. A specimen material solution that includes a particular analyte is made inflow into the sensor part 22 via the fine flow passage 16, and a fluorescence substance that labels an analyte is then made inflow via the fine flow passage 16. By this configuration, an analyte that has been labeled by a fluorescence substance can be fixed to the sensor part 22.

A fluorescence substance is not restricted in particular as long as a fluorescence substance is a substance that is excited and that emits the fluorescence in the case in which a predetermined excitation light is applied or an electrical field effect is utilized. In the present specification, the "fluorescence" includes a wide variety of emissions of lights such as phosphorescence.

A specimen material solution that includes an analyte is not restricted in particular. As such a specimen material, there can be mentioned for instance a blood, a blood serum, a blood plasma, urine, a nasal passage fluid, a saliva, a feces, and a body cavity fluid (such as a spinal fluid, an ascites fluid, and a pleural effusion).

As an analyte that is included in a specimen material, there can be mentioned for instance a nucleic acid (single-stranded or double-stranded DNA, RNA, polynucleotide, oligonucleotide, and PNA (peptide nucleic acid), and nucleoside, nucleotide, and a modified molecule thereof), a protein substance (such as polypeptide and oligopeptide), an amino acid (including a modified amino acid), carbohydrate (such as oligosaccharide, polysaccharide, and a sugar chain), lipid, a modified molecule thereof, and a complex thereof. More specifically, an analyte can also be a carcinoembryonic antigen such as an AFP (α fetoprotein), a tumor marker, a signal transducer, and a hormone, and is not restricted in particular.

A light source 24 is disposed on a side of one side face 12b under the dielectric member 12 as shown in FIG. 1. An excitation light 26 from the light source 24 is incident to the side face 12b of the dielectric member 12 from the outside and the lower side of the dielectric member 12. The excitation light 26 is then applied toward the metallic thin film 14 that has been formed on an upper surface 12a of the dielectric member 12 at a predetermined incidence angle (a resonance angle) α1 by which the attenuated total reflectance (ATR) of the excitation light 26 occurs via the dielectric member 12.

A light detection means 30 that is configured to receive a fluorescence 28 that is emitted by an excitation of a fluorescence substance is disposed over the sensor chip 18.

The light detection means 30 is not restricted in particular. As the light detection means 30, a photomultiplier tube of a photon counting system, a CCD (Charge Coupled Device) image sensor capable of performing a multipoint measurement, and a CMOS (Complementary Metal Oxide Semiconductor) image sensor can be used for instance. In the present embodiment, a photomultiplier tube of a photon counting system is used.

In the present embodiment, as a fluorescence amount adjusting means 32 that is configured to adjust a light amount of a fluorescence that has emitted, a neutral density (ND) filter 34 that is configured to be able to cut a light amount of 99% is disposed between the sensor chip 18 and the light detection means 30 in such a manner that the filter can be moved into or out without any inhibition.

The fluorescence amount adjusting means 32 is not restricted in particular as long as the fluorescence amount adjusting means 32 can adjust an amount of a light that is received for the light detection means 30. For far more than the neutral density (ND) filter 34, a wavelength selective filter or a diaphragm lens can also be disposed in such a manner that the wavelength selective filter or the diaphragm lens can be moved into or out without any inhibition. In addition, an aperture can also be formed and a light amount can be adjusted depending on a size of an opening of the aperture.

In the present embodiment, the fluorescence amount adjusting means 32 can also be made to be a focus adjusting means of the light detection means 30. By defocusing the light detection means 30, an amount of a fluorescence that is received by the light detection means 30 can also be adjusted.

In the present embodiment, an excitation light is applied from the light source 24 is not restricted in particular. However, it is preferable to use an excitation light of a wavelength in the range of 200 to 900 nm and of the range of 0.001 to 1000 mW, more preferably, an excitation light of a wavelength in the range of 230 to 800 nm and of the range of 0.01 to 100 mW.

The dielectric member 12 is not restricted in particular. As the dielectric member 12, a wide variety of inorganic substances such as a glass and a ceramics, natural polymers, and synthetic polymers that are optically transparent can be used. From the aspect of the chemical stability, manufacturing stability, and optical transparency, it is preferable that the dielectric member 12 includes silicon dioxide ($SiO_2$) or titanium dioxide ($TiO_2$).

The dielectric member 12 in a prism shape in which a vertical cross sectional shape is a generally trapezoidal shape is used in the present embodiment. However, a shape of the dielectric member 12 can also be modified in an appropriate manner in such a manner that a vertical cross sectional shape is a triangular shape (so-called a triangular prism), a semicircular shape, and a semi elliptical shape.

A material of the metallic thin film 14 is not restricted in particular. As a material of the metallic thin film 14, the metallic thin film 14 is made of a metal of at least one kind that is selected from a group that is composed of gold, silver, aluminum, copper, and platinum, more preferably gold, and the metallic thin film 14 can also be made of an alloy of the metal.

Such a metal is stable to oxidization and is suitable for the metallic thin film 14 since an electrical field enhancement caused by a surface plasmon light (a crude density wave) is increased as described later.

A method for forming the metallic thin film 14 is not restricted in particular. As a method for forming the metallic thin film 14, there can be mentioned for instance a sputtering method, a vapor deposition method (such as a resistance heating vapor deposition method and an electron beam vapor deposition method), an electrolytic plating method, and an electroless plating method. In particular, a sputtering method and a vapor deposition method are preferable since an adjustment of the condition of a thin film formation can be easily carried out.

A thickness of the metallic thin film 14 is not restricted in particular. As a thickness of the metallic thin film 14, it is preferable that a thickness of gold is in the range of 5 to 500 nm, a thickness of silver is in the range of 5 to 500 nm, a thickness of aluminum is in the range of 5 to 500 nm, a thickness of copper is in the range of 5 to 500 nm, a thickness of platinum is in the range of 5 to 500 nm, and a thickness of an alloy of the metal is in the range of 5 to 500 nm.

From the aspect of an electrical field enhancement effect as described later, as a more preferable thickness of the metallic thin film 14, it is more preferable that a thickness of gold is in the range of 20 to 70 nm, a thickness of silver is in the range of 20 to 70 nm, a thickness of aluminum is in the range of 10 to 50 nm, a thickness of copper is in the range of 20 to 70 nm, a thickness of platinum is in the range of 20 to 70 nm, and a thickness of an alloy of the metal is in the range of 20 to 70 nm.

In the case in which a thickness of the metallic thin film 14 is in the range described above, the thickness is suitable since a surface plasmon light (a crude density waven) described later is easily generated. For the metallic thin film 14 that is provided with such a thickness, the dimensions and a shape of a size (vertical length×horizontal length) are not restricted in particular.

1-2. Method for Measuring a Fluorescence Amount

A surface plasmon-field enhanced fluorescence spectroscopic measurement method using the SPFS apparatus 10 in accordance with the present invention that is configured as described above will be described in accordance with the flowchart shown in FIG. 3.

In the first place, a specimen material solution that includes a particular analyte is made inflow into the sensor part 22 via the fine flow passage 16, and a fluorescence substance that labels the analyte is then made inflow via the fine flow passage 16 similarly. By this configuration, an analyte that has been labeled by a fluorescence substance is fixed to the sensor part 22.

An excitation light 26 is applied from the light source 24 in this state, and the excitation light 26 is incident to the side face 12b of the dielectric member 12 from the outside and the lower side of the dielectric member 12. The excitation light 26 is then applied toward the metallic thin film 14 that has been formed on an upper surface 12a of the dielectric member 12 at a predetermined incidence angle (a resonance angle) α1 by which the attenuated total reflectance (ATR) of the excitation light 26 occurs via the dielectric member 12.

By applying the excitation light 26, a surface plasmon light (a crude density waven) is emitted from the surface of the metallic thin film 14, and a fluorescence substance that labels the analyte, which has been fixed to the sensor part 22, is excited by the surface plasmon light (a crude density waven), thereby emitting a fluorescence 28.

At this time, the fluorescence amount adjusting means 32 is in the state in which a light intensity is not reduced, that is, the neutral density (ND) filter 34 is not inserted between the sensor chip 18 and the light detection means 30 (a first condition).

By detecting the fluorescence 28 by using the light detection means 30, the analyte that has been fixed to the sensor part 22 is detected and a fluorescence signal in accordance with a concentration of an analyte (a first fluorescence signal) is output from the light detection means 30.

In the next place, in the state in which a light intensity is reduced by the fluorescence amount adjusting means 32, that is, the neutral density (ND) filter 34 is inserted between the sensor chip 18 and the light detection means 30 (a second condition), the fluorescence 28 is detected by using the light detection means 30. As a result, a second fluorescence signal is output from the light detection means 30.

By reducing a light by the fluorescence amount adjusting means 32, the fluorescence 28 that is received by the light detection means 30 becomes 1/100 as compared with the state in which a light intensity is not reduced. Consequently, in the case in which the light detection means 30 receives the fluorescence 28 in a normal way, the second fluorescence signal also becomes 1/100 as compared with the first fluorescence signal that is output in the state in which a light intensity is not reduced.

Based on this, in the case in which the second fluorescence signal in the state in which a light intensity is reduced is larger than 1/100 of the first fluorescence signal in the state in which a light intensity is not reduced, an accurate fluorescence signal can be obtained by correcting the second fluorescence signal in the state in which a light intensity is reduced as described later.

1-3. Correction of a Fluorescence Signal

Figure 4:
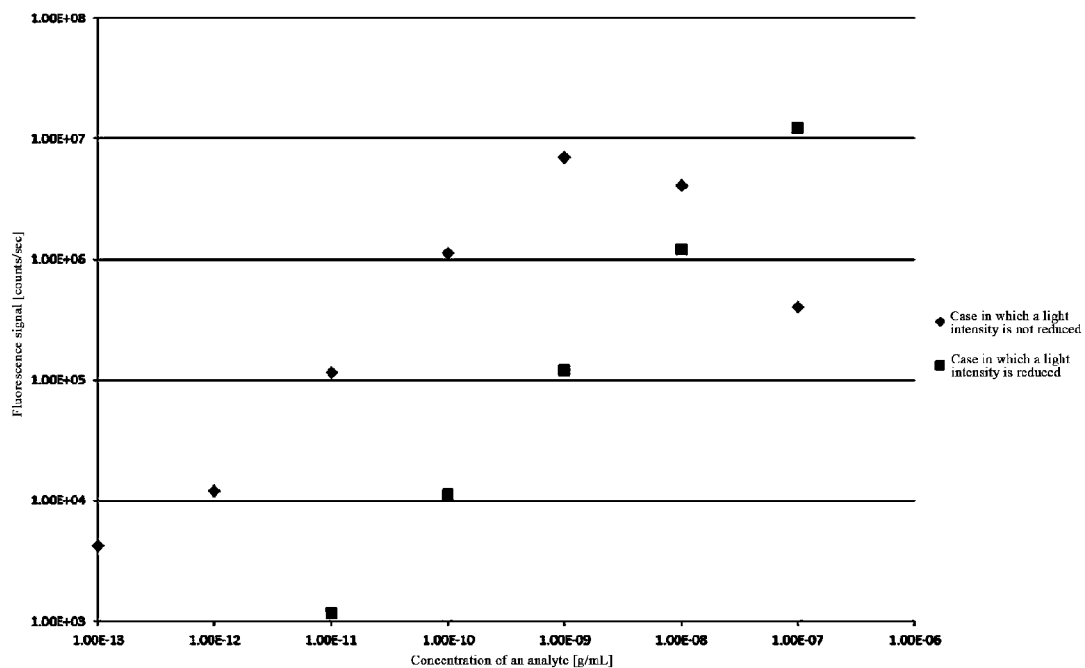
FIG. 4 is a graph for showing the relationship between a concentration of an analyte and a fluorescence signal that is output from a light detection means 30 in a state in which a light intensity is not reduced and a fluorescence signal that is output from a light detection means 30 in a state in which a light intensity is reduced.

Table 1 shows the relationship between a concentration of an analyte and a fluorescence signal that is output by the light detection means 30 in the state in which a light intensity is not reduced and a fluorescence signal that is output by the light detection means 30 in the state in which a light intensity is reduced. FIG. 4 is a graph indicating the relationship of Table 1.

TABLE 1

Concentration of an analyte [g/mL]
Fluorescence signal [counts/sec]
Light intensity is not reduced
Light intensity is reduced As shown in Table 1 and FIG. 4, in the case in which a light intensity is not reduced by the fluorescence amount adjusting means 32, the higher a concentration of an analyte is, the lower a level of a fluorescence signal is by contraries.

The judgment of a reduction of a fluorescence signal is carried out based on that a fluorescence signal in the case in which a light intensity is reduced by the fluorescence amount adjusting means 32 becomes 1/100 as compared with a fluorescence signal in which a light intensity is not reduced as described above.

In other words, in the present embodiment, in the case in which a concentration of an analyte is high, that is, in the range of 1.0E-9 to 1.0E-7 (g/mL), a fluorescence signal in the case in which a light intensity is reduced is larger than 1/100 of a fluorescence signal in the case in which a light intensity is not reduced.

In this case, an accurate value of a fluorescence signal can be obtained by correcting a value while using a fluorescence signal in the case in which a light intensity is reduced (in the present embodiment, a value of a fluorescence signal in the case in which a light intensity is reduced is centupled).

On the other hand, in the case in which a concentration of an analyte is low, that is, in the range of 1.0E-13 to 1.0E-12 (g/mL), a fluorescence signal in the case in which a light intensity is reduced is also larger than 1/100 of a fluorescence signal in the case in which a light intensity is not reduced. This is caused by the lowest value of a light amount that can be measured by the light detection means 30, and this is because a fluorescence signal in the case in which a light intensity is reduced outputs an abnormal value.

Consequently, in the case in which a concentration of an analyte is low, a fluorescence signal in the case in which a light intensity is not reduced can be obtained as a normal value.

Figure 5:
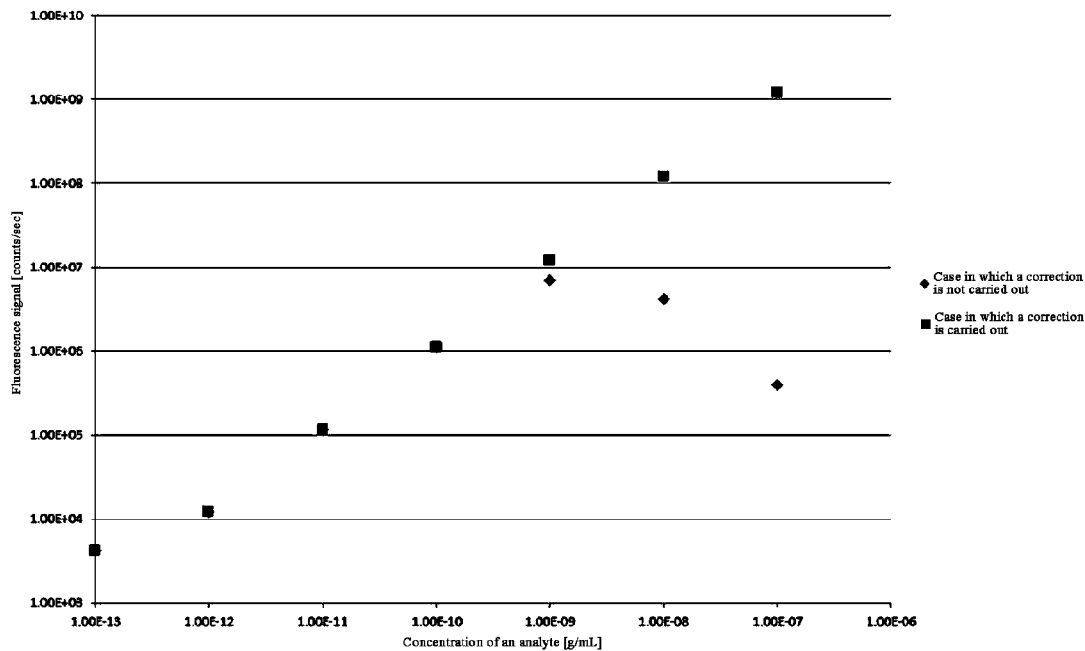
FIG. 5 is a graph for showing the relationship between a concentration of an analyte and a fluorescence signal that is output from a light detection means 30 in a state in which a correction is not carried out and a fluorescence signal that is output from a light detection means 30 in a state in which a correction is carried out.

As described above, a normal measurement of a concentration of an analyte can be carried out by using a corrected fluorescence signal as shown in Table 2 and FIG. 5.

TABLE 2

Concentration of an analyte [g/mL]
Fluorescence signal [counts/sec]
Correction is not carried out
Correction is carried out Embodiment 2

2. Embodiment in the Case in which an Amount of an Excitation Light is Adjusted

Figure 6:
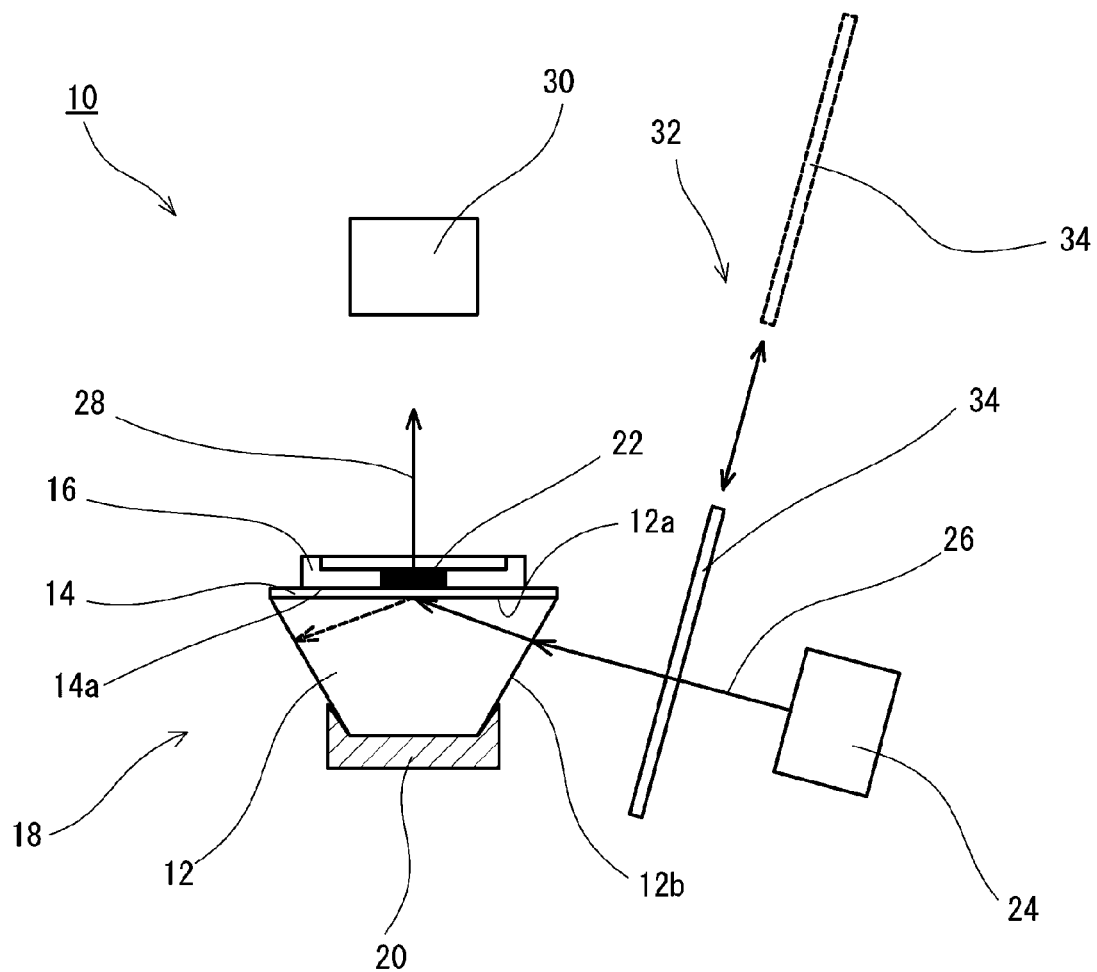
FIG. 6 is a schematic plan view showing a frame format of a simple overview of an SPFS apparatus for describing a surface plasmon-field enhanced fluorescence spectroscopic measurement method in accordance with an embodiment of the present invention.

FIG. 6 is a schematic plan view showing a frame format of a simple overview of an SPFS apparatus for describing a surface plasmon-field enhanced fluorescence spectroscopic measurement method in accordance with an embodiment of the present invention.

The SPFS apparatus 10 of the modified example is provided with a configuration that is equivalent to that of the SPFS apparatus shown in FIGS. 1 to 5 in a basic way and the principle of the SPFS apparatus 10 is also equivalent to that of the SPFS apparatus shown in FIGS. 1 to 5 in a basic way. Consequently, constitutive members that are equivalent to those illustrated in FIGS. 1 to 5 are numerically numbered similarly and the detailed descriptions of the equivalent constitutive members are omitted.

2-1. Configuration of the SPFS Apparatus

As shown in FIG. 6, the modified example is provided with a fluorescence amount adjusting means 32 between a light source 24 and a sensor chip 18. By this configuration, a light amount of an excitation light 26 that is applied from the light source 24 to the metallic thin film 14 can be adjusted (reduced), and as a result, the intensity of an electrical field by a surface plasmon light that is generated on the surface of the metallic thin film 14 can be reduced.

Consequently, a light amount of a fluorescence that is emitted from a fluorescence substance that labels an analyte can be adjusted, and similarly to the embodiment 1, a light amount of a fluorescence that is received by the light detection means 30 can be adjusted. Moreover, a fluorescence signal in accordance with a concentration of an analyte can be obtained by using a measurement method of a light amount of the fluorescence similar to the embodiment 1

In the case of the present embodiment, the fluorescence amount adjusting means 32 can also be made to be a light amount adjusting function of the light source 24, and a light amount of a fluorescence 26 that is emitted from the light source 24 can also be adjusted.

2-2. Correction of a Fluorescence Signal

Figure 7:
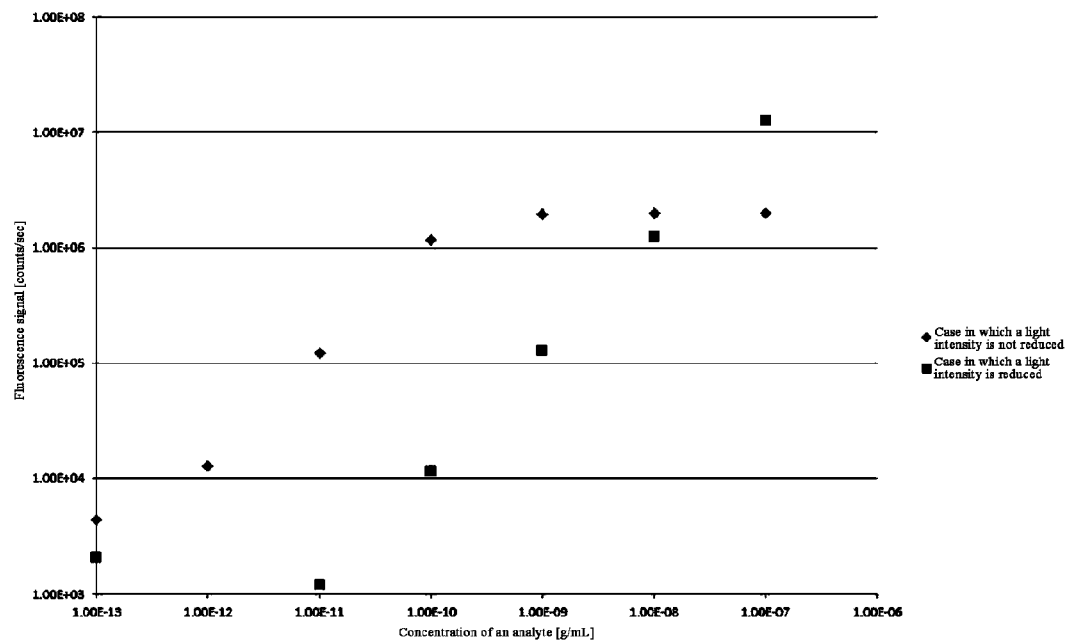
FIG. 7 is a graph for showing the relationship between a concentration of an analyte and a fluorescence signal that is output from a light detection means 30 in a state in which a light intensity is not reduced and a fluorescence signal that is output from a light detection means 30 in a state in which a light intensity is reduced.

Table 3 shows the relationship between a concentration of an analyte and a fluorescence signal that is output by the light detection means 30 in the state in which a light intensity is not reduced and a fluorescence signal that is output by the light detection means 30 in the state in which a light intensity is reduced. FIG. 7 is a graph indicating the relationship of Table 3.

TABLE 3

Concentration of an analyte [g/mL]
Fluorescence signal [counts/sec]
Light intensity is not reduced
Light intensity is reduced As shown in Table 3 and FIG. 7, in the case in which an excitation light is not reduced by the fluorescence amount adjusting means 32, as a concentration of an analyte is higher, a plateaued abnormal output is generated.

The judgment of an abnormal output of a fluorescence signal is carried out based on that a fluorescence signal in the case in which a light intensity is reduced by the fluorescence amount adjusting means 32 becomes 1/100 as compared with a fluorescence signal in which a light intensity is not reduced similarly to the embodiment 1.

In other words, in the present embodiment, in the case in which a concentration of an analyte is high, that is, in the range of 1.0E-9 to 1.0E-7 (g/mL), a fluorescence signal in the case in which a light intensity is reduced is larger than 1/100 of a fluorescence signal in the case in which a light intensity is not reduced.

In this case, an accurate value of a fluorescence signal can be obtained by correcting a value while using a fluorescence signal in the case in which a light intensity is reduced (in the present embodiment, a value of a fluorescence signal in the case in which a light intensity is reduced is centupled).

On the other hand, in the case in which a concentration of an analyte is low, that is, in the range of 1.0E-13 to 1.0E-12 (g/mL), a fluorescence signal in the case in which a light intensity is reduced is also larger than 1/100 of a fluorescence signal in the case in which a light intensity is not reduced. This is caused by the lowest value of a light amount that can be measured by the light detection means 30, and this is because a fluorescence signal in the case in which a light intensity is reduced outputs an abnormal value.

Consequently, in the case in which a concentration of an analyte is low, a fluorescence signal in the case in which a light intensity is not reduced can be obtained as a normal value.

Figure 8:
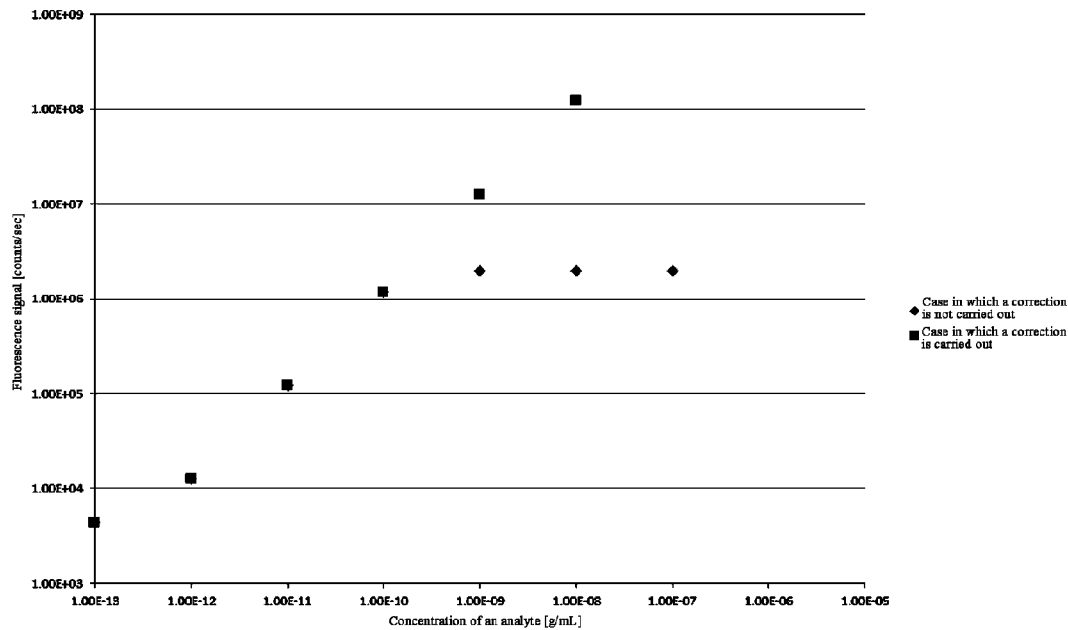
FIG. 8 is a graph for showing the relationship between a concentration of an analyte and a fluorescence signal that is output from a light detection means 30 in a state in which a correction is not carried out and a fluorescence signal that is output from a light detection means 30 in a state in which a correction is carried out.

As described above, a normal measurement of a concentration of an analyte can be carried out by using a corrected fluorescence signal as shown in Table 4 and FIG. 8.

TABLE 4

Concentration of an analyte [g/mL]
Fluorescence signal [counts/sec]
Correction is not carried out
Correction is carried out

Embodiment 3

3. Embodiment in the Case in which a Light Amount of a Fluorescence that has been Generated and an Amount of an Excitation Light are Adjusted FIG. 9 is a schematic plan view showing a frame format of a simple overview of an SPFS apparatus for describing a surface plasmon-field enhanced fluorescence spectroscopic measurement method in accordance with an embodiment of the present invention.

The SPFS apparatus 10 of the modified example is provided with a configuration that is equivalent to that of the SPFS apparatus shown in FIGS. 1 to 5 in a basic way and the principle of the SPFS apparatus 10 is also equivalent to that of the SPFS apparatus shown in FIGS. 1 to 5 in a basic way. Consequently, constitutive members that are equivalent to those illustrated in FIGS. 1 to 5 are numerically numbered similarly and the detailed descriptions of the equivalent constitutive members are omitted.

3-1. Configuration of the SPFS Apparatus

Figure 9:
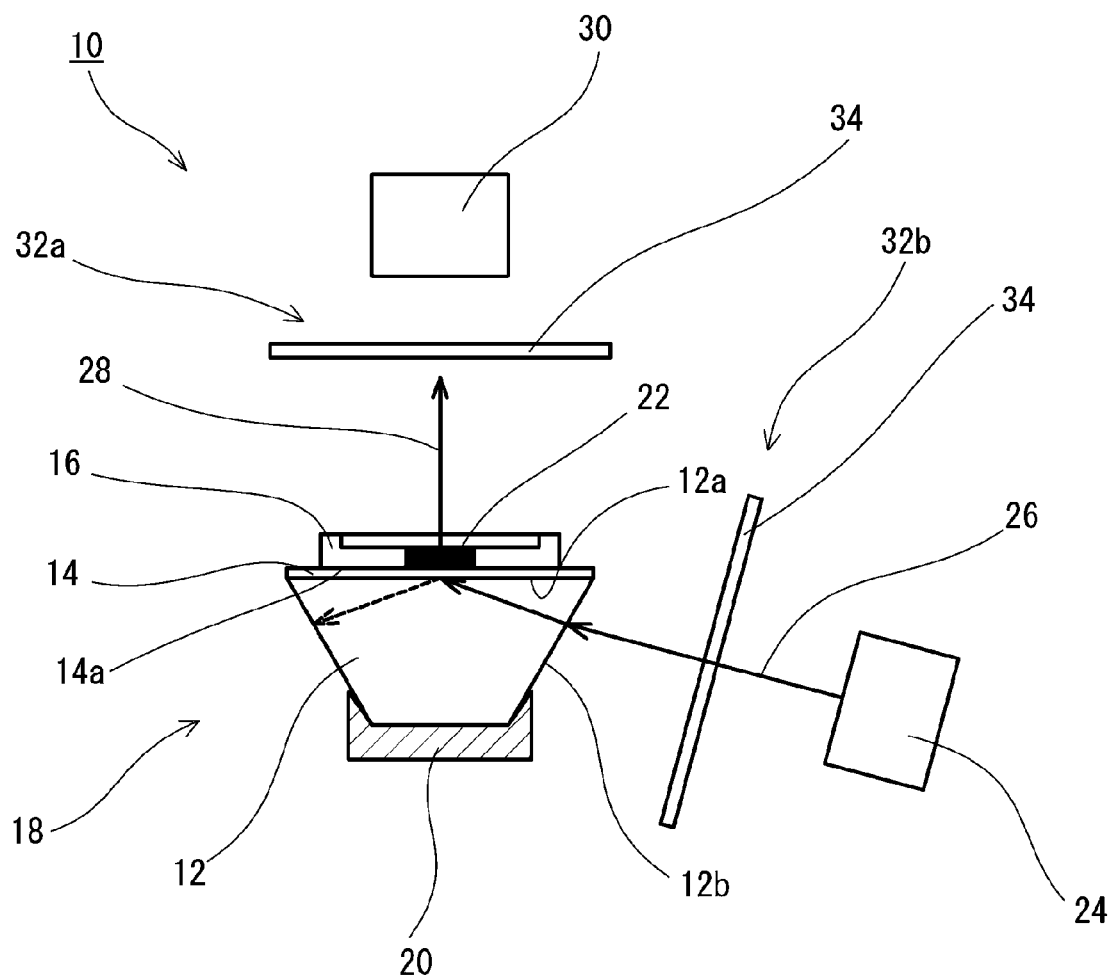
FIG. 9 is a schematic plan view showing a frame format of a simple overview of an SPFS apparatus for describing a surface plasmon-field enhanced fluorescence spectroscopic measurement method in accordance with an embodiment of the present invention.

As shown in FIG. 9, the modified example is provided with a fluorescence amount adjusting means (a fluorescence amount adjusting means 32a) between a sensor chip 18 and a light detection means 30, and a fluorescence amount adjusting means (a fluorescence amount adjusting means 32b) between a light source 24 and a sensor chip 18.

By this configuration, a light amount of a fluorescence that is emitted from a fluorescence substance that labels an analyte can be adjusted by the fluorescence amount adjusting means 32a, and a light amount of an excitation light 26 that is applied from the light source 24 to the metallic thin film 14 can be adjusted.

In addition to an adjustment of a light amount of a fluorescence that is generated, by adjusting a light amount of an excitation light 26 that is caused by a generation of a fluorescence 28, a wider dynamic range can be provided.

For the SPFS apparatus 10 in accordance with the present invention that is configured as described above, similarly to the embodiments 1 and 2, by detecting an analyte that has been fixed to the sensor part 22 while adjusting a light amount of a fluorescence, a fluorescence signal in a wider dynamic range can be obtained, and a measurement of a specimen material solution that is provided with a concentration of an analyte in a wider range is carried out.

Embodiment 4

4. Embodiment in the Case in which a Light Source is Provided with an Application Angle Adjusting Means FIG. 10 is a schematic plan view showing a frame format of a simple overview of an SPFS apparatus for describing a surface plasmon-field enhanced fluorescence spectroscopic measurement method in accordance with an embodiment of the present invention.

The SPFS apparatus 10 of the modified example is provided with a configuration that is equivalent to that of the SPFS apparatus shown in FIGS. 1 to 5 in a basic way and the principle of the SPFS apparatus 10 is also equivalent to that of the SPFS apparatus shown in FIGS. 1 to 5 in a basic way. Consequently, constitutive members that are equivalent to those illustrated in FIGS. 1 to 5 are numerically numbered similarly and the detailed descriptions of the equivalent constitutive members are omitted.

4-1. Configuration of the SPFS Apparatus

Figure 10:
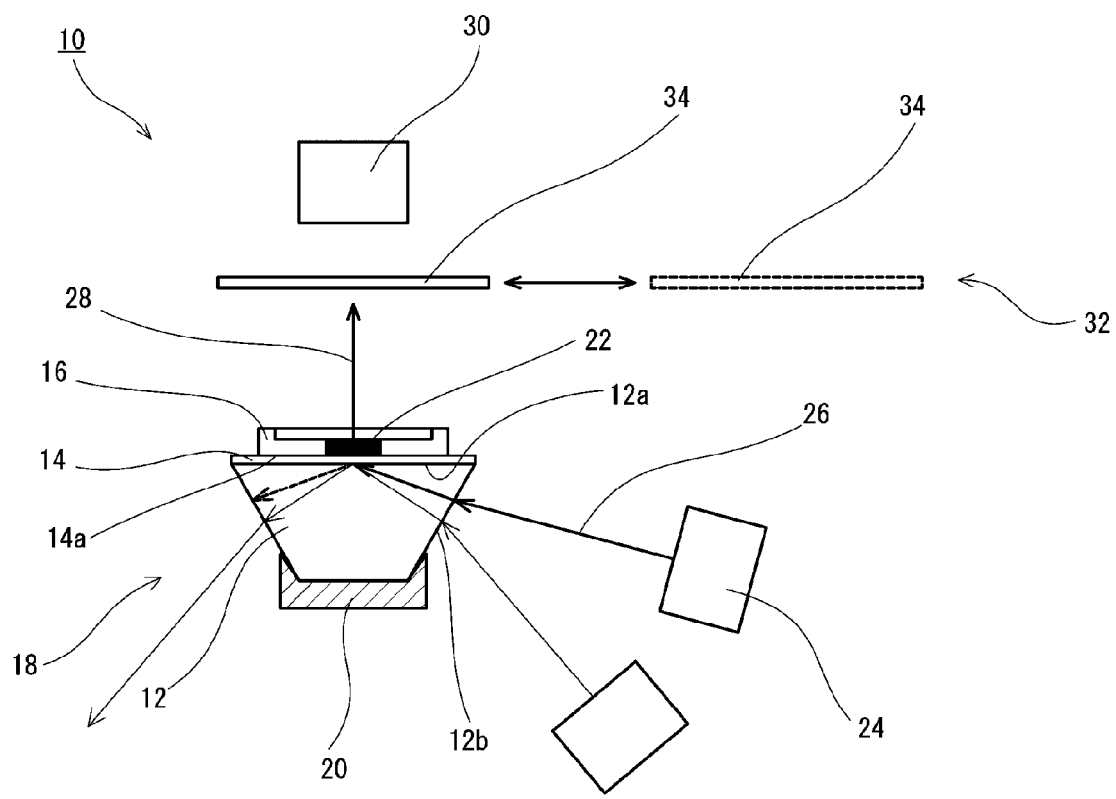
FIG. 10 is a schematic plan view showing a frame format of a simple overview of an SPFS apparatus for describing a surface plasmon-field enhanced fluorescence spectroscopic measurement method in accordance with an embodiment of the present invention.
Figure 11:
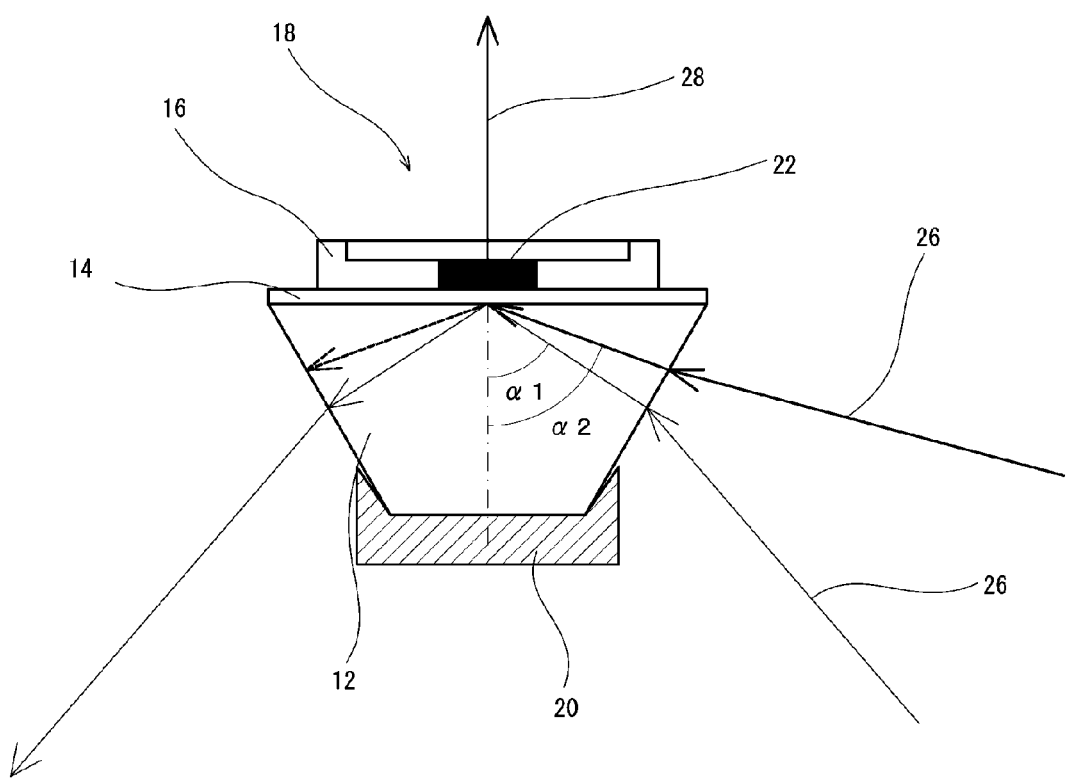
FIG. 11 is a partially enlarged view of FIG. 10.

As shown in FIG. 10, the modified example is provided with an application angle adjusting means that is configured to be able to change an incidence angle of the excitation light 26 that is applied toward the metallic thin film 14 to the metallic thin film 14 via the dielectric member 12 from the light source 24.

Figure 12:
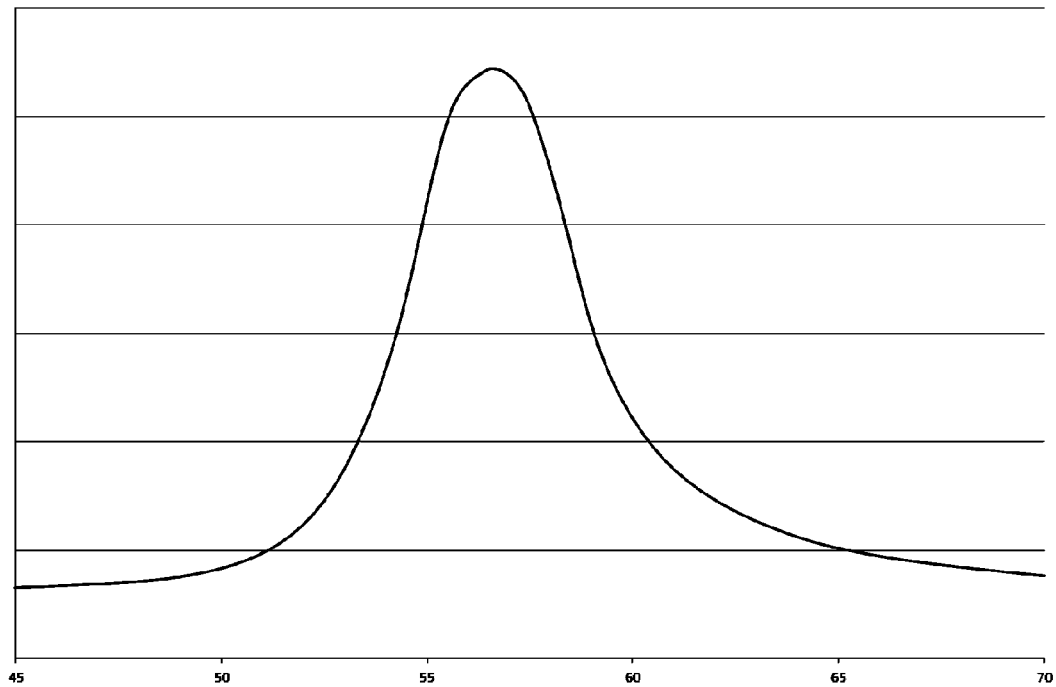
FIG. 12 is a graph for showing the relationship between an incidence angle of an excitation light and a fluorescence signal in the case in which a specimen material solution that is provided with a low concentration of an analyte is measured.

In general, it is known that an angle dependency as shown in FIG. 12 exists for an incidence angle to the metallic thin film 14 and a fluorescence signal.

In the present embodiment, a light amount of the fluorescence can be reduced by making an incidence angle of the excitation light 26 to the metallic thin film 14 smaller than a resonance angle (that is, an angle by which the attenuated total reflectance (ATR) of the excitation light 26 occurs) or making the incidence angle larger than the resonance angle based on the angle dependency.

4-2. Correction of a Fluorescence Signal

In the case in which the light source 24 is provided with an application angle adjusting means like the modified example, an incidence angle as described above can also be used for judging an abnormal output of a fluorescence signal.

In other words, in the case in which a detection of an analyte is carried out, by obtaining a fluorescence signal while changing an incidence angle of the excitation light 26 in a predetermined range (in the present embodiment, in a range of 45° to 70°), a relationship between an incidence angle of the excitation light and a fluorescence signal can be obtained as shown in FIG. 12.

Figure 13:
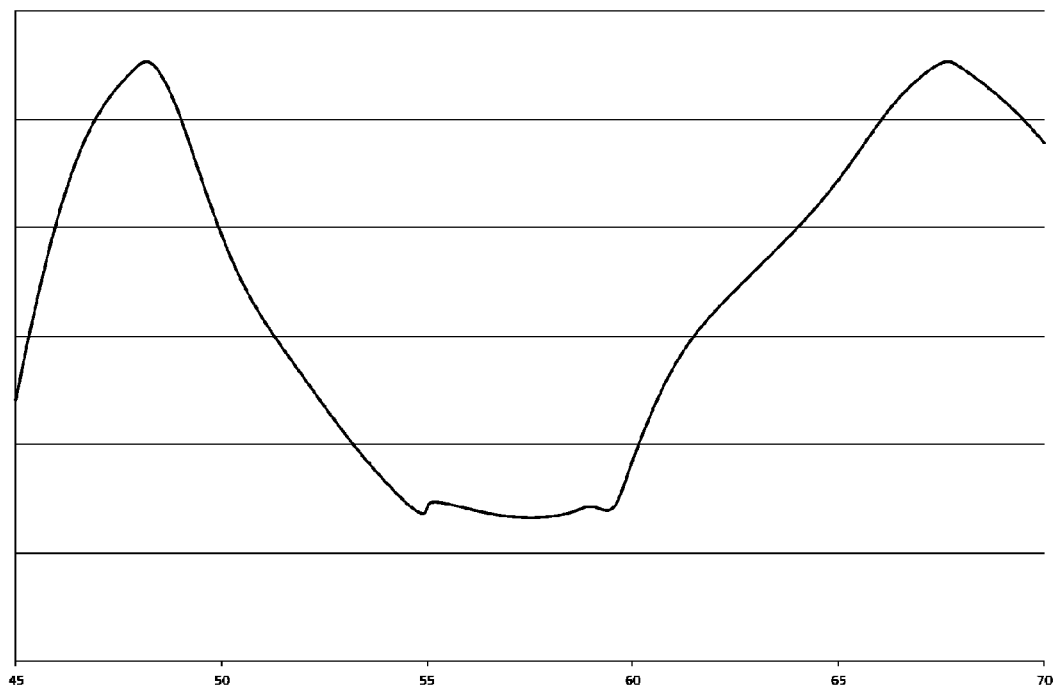
FIG. 13 is a graph for showing the relationship between an incidence angle of an excitation light and a fluorescence signal in the case in which a specimen material solution that is provided with a high concentration of an analyte is measured.
Figures 14, 15:
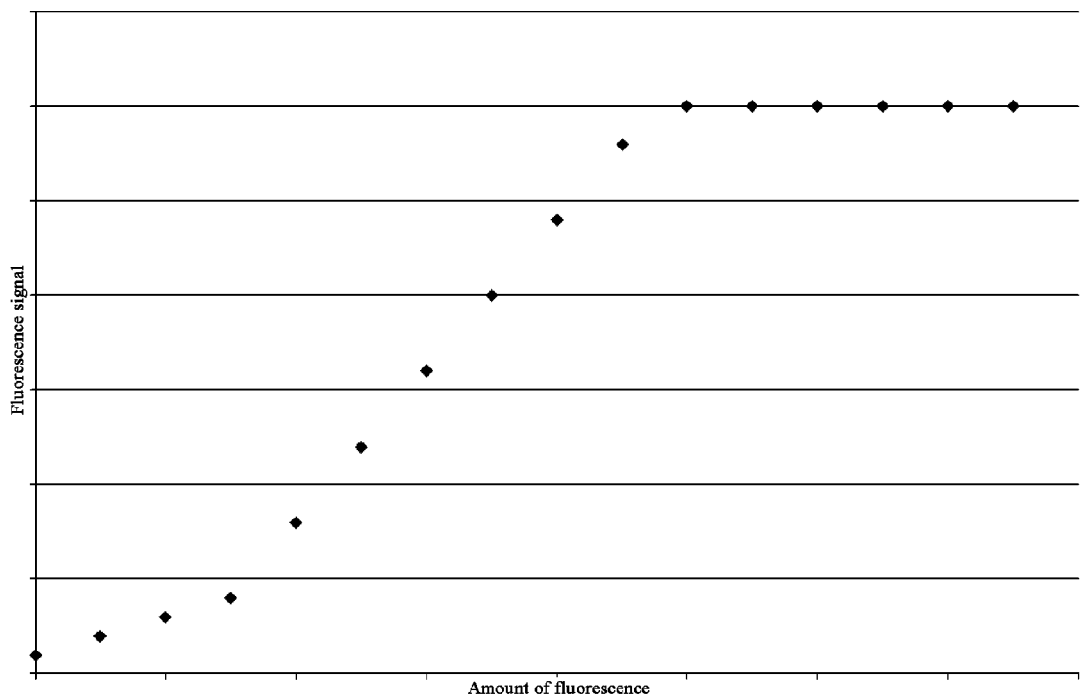
FIG. 14 is a graph for showing the relationship between a light amount of a received fluorescence and a fluorescence signal in the case in which a CCD camera is used.
FIG. 15 is a graph for showing the relationship between a light amount of a received fluorescence and a fluorescence signal in the case in which a photomultiplier tube of a photon counting system is used.

Under normal conditions, as a concentration of an analyte becomes higher, a fluorescence signal is increased. However, in the case in which a concentration of an analyte becomes high and a light amount of a fluorescence that is emitted exceeds a dynamic range of the light detection means 30, an abnormal fluorescence signal is obtained in such a manner that a plurality of peaks are generated as shown in FIG. 13.

In the case in which an abnormal fluorescence signal is obtained, similarly to the embodiments 1 to 3, a detection of an analyte that is provided with a wide dynamic range can be carried out in a precise manner by correcting a fluorescence signal that has been obtained in the case in which a light amount of a fluorescence that is received by the light detection means 30 is reduced by using the fluorescence amount adjusting means 32.

While the preferred embodiments in accordance with the present invention have been described above, the present invention is not restricted to the embodiments described above. In the above described embodiment for instance, a light intensity is reduced by the fluorescence amount adjusting means 32 in such a manner that a light amount of the fluorescence 28 that is received by the light detection means 30 becomes 1/100. However, some changes can be carried out in an appropriate manner in accordance with a dynamic range that is required, and various changes, modifications, and functional additions can be thus made without departing from the scope of the present invention.

INDUSTRIAL APPLICABILITY the present invention, a detection of an analyte that is provided with a wide dynamic range can be carried out in a precise manner in a field in which a detection of a higher degree of accuracy is required such as a clinical trial of a blood test or the like using a surface-plasmon enhanced fluorescence spectroscopy (SPFS) for instance.

REFERENCE SIGNS LIST

10: SPFS apparatus
12: Dielectric member

12a: Upper surface
12b: Side surface
14: Metallic thin film
14a: Upper surface
16: Fine flow passage
18: Sensor chip
20: Sensor chip mounting part
22: Sensor part
24: Light source
26: Excitation light
28: Fluorescence
30: Light detection means
32: Fluorescence amount adjusting means
32a: Fluorescence amount adjusting means
32b: Fluorescence amount adjusting means
34: Filter

The invention claimed is:

1. A surface plasmon-field enhanced fluorescence stereoscopic measurement method comprising:
  exciting a fluorescence substance that has labeled an analyte by surface plasmon light that has been generated by applying an excitation light to a metallic thin film and receiving the generated fluorescence by a light detection means to thereby detect the analyte;
  by comparing a first fluorescence signal that is output in the case in which the light detection means receives a fluorescence under a first condition and a second fluorescence signal that is output in the case in which the light detection means receives a fluorescence in which a light amount has been adjusted under a second condition in which a light amount of a fluorescence that is received by the light detection means is adjusted so as to be smaller than that in the first condition, judging whether or not the first fluorescence signal is abnormal; and
  obtaining a normal fluorescence signal by correcting the second fluorescence signal in the case in which it is decided that the first fluorescence signal is abnormal.

2. The surface plasmon-field enhanced fluorescence stereoscopic measurement method as defined in claim 1, further comprising the step of adjusting a light amount of a fluorescence that is received by the light detection means by adjusting a light amount of the fluorescence that has been generated.

3. The surface plasmon-field enhanced fluorescence stereoscopic measurement method as defined in claim 1, further comprising the step of adjusting a light amount of a fluorescence that is received by the light detection means by adjusting a light amount of the excitation light.

4. The surface plasmon-field enhanced fluorescence stereoscopic measurement method as defined in claim 1, further comprising the step of:
  receiving a fluorescence by the light detection means while changing an incidence angle of the excitation light to the metallic thin film in a predetermined range; and
  judging an abnormal fluorescence signal based on the relationship between an incidence angle of the excitation light and a fluorescence signal that is output in the case in which the light detection means receives a fluorescence.

5. A surface plasmon-field enhanced fluorescence spectroscopic measurement apparatus that is configured to carry out a detection of a specimen material by applying an excitation light, in which a metallic thin film that is formed on a dielectric member, a fine flow passage that is formed on an upper surface of the metallic thin film, and a sensor chip that is provided with a sensor part that is formed in the fine flow passage are mounted, comprising:
  a light source that is configured to apply an excitation light to the metallic thin film via the dielectric member; and
  a light detection means that is disposed over the sensor chip,
  wherein the light detection means is configured to receive a fluorescence that is generated by exciting a fluorescence substance that labels an analyte that is fixed to the sensor part by a surface plasmon light that is generated in the case in which the excitation light is applied to the metallic thin film;
  a fluorescence amount adjusting means is configured to be able to adjust a light amount of a fluorescence that is received by the light detection means; and
  the fluorescence amount adjusting means is disposed between the sensor chip and the light detection means.

6. The surface plasmon-field enhanced fluorescence spectroscopic measurement apparatus as defined in claim 5, wherein:
  by comparing a first fluorescence signal that is output in the case in which the light detection means receives a fluorescence under a first condition and a second fluorescence signal that is output in the case in which the light detection means receives a fluorescence in which a light amount has been adjusted by the fluorescence amount adjusting means under a second condition in which a light amount of a fluorescence that is received by the light detection means is adjusted so as to be smaller than that in the first condition, it is judged whether or not the first fluorescence signal is abnormal; and
  a normal fluorescence signal is obtained by correcting the second fluorescence signal in the case in which it is decided that the first fluorescence signal is abnormal.

7. The surface plasmon-field enhanced fluorescence spectroscopic measurement apparatus as defined in claim 5, further comprising an application angle adjusting means that is configured to adjust an incidence angle of the excitation light to the metallic thin film.

8. The surface plasmon-field enhanced fluorescence spectroscopic measurement apparatus as defined in claim 5, wherein:
  a fluorescence is received by the light detection means while changing an incidence angle of the excitation light to the metallic thin film in a predetermined range by using the application angle adjusting means; and
an abnormal fluorescence signal is judged based on the relationship between an incidence angle of the excitation light and a fluorescence signal that is output in the case in which the light detection means receives a fluorescence.

9. A surface plasmon-field enhanced fluorescence spectroscopic measurement apparatus that is configured to carry out a detection of a specimen material by applying an excitation light, in which a metallic thin film that is formed on a dielectric member, a fine flow passage that is formed on an upper surface of the metallic thin film, and a sensor chip that is provided with a sensor part that is formed in the fine flow passage are mounted, comprising:
  a light source that is configured to apply an excitation light to the metallic thin film via the dielectric member; and
  a light detection means that is disposed over the sensor chip,
  wherein the light detection means is configured to receive a fluorescence that is generated by exciting a fluorescence substance that labels an analyte that is fixed to the sensor part by a surface plasmon light that is generated in the case in which the excitation light is applied to the metallic thin film;

a fluorescence amount adjusting means is configured to be able to adjust a light amount of a fluorescence that is received by the light detection means; and the fluorescence amount adjusting means is disposed between the light source and the dielectric member.

10. The surface plasmon-field enhanced fluorescence spectroscopic measurement apparatus as defined in claim 9, wherein:

by comparing a first fluorescence signal that is output in the case in which the light detection means receives a fluorescence under a first condition and a second fluorescence signal that is output in the case in which the light detection means receives a fluorescence in which a light amount has been adjusted by the fluorescence amount adjusting means under a second condition in which a light amount of a fluorescence that is received by the light detection means is adjusted so as to be smaller than that in the first condition, it is judged whether or not the first fluorescence signal is abnormal; and a normal fluorescence signal is obtained by correcting the second fluorescence signal in the case in which it is decided that the first fluorescence signal is abnormal.

\* \* \* \* \*

UNITED STATES PATENT AND TRADEMARK OFFICE
CERTIFICATE OF CORRECTION

PATENT NO. : 9,068,945 B2  
APPLICATION NO. : 14/126752  
DATED : June 30, 2015  
INVENTOR(S) : Naoki Hikage, Masataka Matsuo and Takatoshi Kaya Page 1 of 1

It is certified that error appears in the above-identified patent and that said Letters Patent is hereby corrected as shown below:

Title page, item 75 inventors, should read: Naoki Hikage, Hachioji-shi (JP); Masataka Matsuo, Hachioji-shi, (JP); and Takatoshi Kaya, Inagi-shi (JP).

Signed and Sealed this  
Eighth Day of December, 2015

Michelle K. Lee  
*Director of the United States Patent and Trademark Office*